United States Patent [19]

Bjornvad et al.

[11] Patent Number: 6,060,274
[45] Date of Patent: May 9, 2000

[54] EXTRACELLULAR EXPRESSION OF CELLULOSE BINDING DOMAINS (CBD) USING BACILLUS

[75] Inventors: Mads Eskelund Bjornvad, Frederiksberg; Martin Schulein, Kobenhavn O; Per Lina Jorgensen, Kobenhavn K, all of Denmark

[73] Assignee: Novo Nordisk A/S, Bagsvaerd, Denmark

[21] Appl. No.: 08/959,212

[22] Filed: Oct. 28, 1997

[30] Foreign Application Priority Data

Oct. 28, 1996 [DK] Denmark .................................. 1192/96
Dec. 13, 1996 [DK] Denmark .................................. 1426/96

[51] Int. Cl.[7] .............................. C12P 21/06; C12N 1/20; C12N 15/00
[52] U.S. Cl. ...................................... 435/69.1; 435/252.31; 435/320.1
[58] Field of Search .............................. 435/252.31, 69.1, 435/71.2; 536/23.1, 23.4

[56] References Cited

U.S. PATENT DOCUMENTS

| | | | |
|---|---|---|---|
| 5,491,084 | 2/1996 | Chalfie et al. | 435/189 |
| 5,525,193 | 6/1996 | Franks et al. | 162/5 |
| 5,536,655 | 7/1996 | Thomas et al. | 435/209 |
| 5,578,489 | 11/1996 | Petersen | 435/263 |

FOREIGN PATENT DOCUMENTS

| | | |
|---|---|---|
| WO 90/00609 | 1/1990 | WIPO . |
| WO 91/10732 | 7/1991 | WIPO . |
| WO 91/17244 | 11/1991 | WIPO . |
| WO 93/05226 | 3/1993 | WIPO . |
| WO 93/11249 | 6/1993 | WIPO . |
| WO 94/07998 | 4/1994 | WIPO . |
| WO 94/24158 | 10/1994 | WIPO . |
| WO 95/16782 | 6/1995 | WIPO . |
| WO 96/13524 | 5/1996 | WIPO . |
| WO 96/34092 | 10/1996 | WIPO . |
| WO 97/28243 | 8/1997 | WIPO . |
| WO 97/28256 | 8/1997 | WIPO . |

OTHER PUBLICATIONS

Creighton, T.E. Proteins: Structures and Molecular Properties, 2nd edition. W.H. Freeman and Company, New York, pp. 23–28, 1993.

Hansen et al. celA from *Bacillus lautus* PL236 encodes a novel cellulose–binding endo–beta–1,4–glucanase. J. Bacteriol. 174(11):3522–3531, Jun. 1992.

Rapoport et al. Gene expression and using *Bacillus*. Current Opinion in Biotechnology 1:21–27, 1990.

Gasson. Progress and potential in the biotechnology of lactic acid bacteria. FEMS Microbiology Reviews 12:3–20, 1993.

Chalfie et al., Science, vol. 263, pp. 802–805 (Feb. 11, 1994).

*Primary Examiner*—Karen Cochrane Carlson
*Assistant Examiner*—Devesh Srivastava
*Attorney, Agent, or Firm*—Steve T. Zelson, Esq.; Reza Green, Esq.

[57] ABSTRACT

The present invention relates to Bacillus hosts transformed with a vector comprising a DNA sequence encoding for a cellulose binding domain (CBD) and capable of expressing said sequence, the expressed polypeptide protein consisting essentially of one or more non-catalytic domains; the cellulose binding domain having a molecular weight in the range of from 4 kD to 35 kD and being obtainable from a microorganism or from a plant, preferably from a bacterium or a fungus; the Bacillus host e.g. being one of the species *Bacillus subtilis, Bacillus licheniformis, Bacillus megaterium, Bacillus stearothermophilos,* and *Bacillus amyloliquefaciens;* and a Bacillus expression vector carrying an inserted DNA sequence encoding for a cellulose binding domain; and a method for producing a cellulose binding domain polypeptide in a Bacillus host cell.

20 Claims, 2 Drawing Sheets

EXTRACELLULAR EXPRESSION OF CELLULOSE BINDING DOMAINS (CBD) USING BACILLUS

CROSS-REFERENCE TO RELATED APPLICATIONS

This application claims priority under 35 U.S.C. 119 of Danish application serial nos. 1192/96 filed Oct. 28, 1996 and 1426/96 filed Dec. 13, 1996, the contents of which are fully incorporated herein by reference.

BACKGROUND OF THE INVENTION

1. Field of the Invention

The present invention relates to a transformed Bacillus host capable of expressing a cellulose binding domain polypeptide, a Bacillus expression vector, and a method for producing a cellulose binding domain in a Bacillus host cell.

2. Description of Related Art

Focus on the CBD as a functional domain has involved the synthesis of the domain as a single domain molecule.

One of the first pure CBD's was obtained as synthesized by automated solid phase synthesis (Kraulis P. et al. (1989)).

It has been shown that CBDs can be expressed in E. coli as functional single domains, see e.g.: Ong E. et al. (1993), wherein it is disclosed that expression using E. coli results in a yield of 33 mg CBD per liter of culture fluid in the periplasma of the cells.

Recently, a double fungal CBD (a dimer) has also succesfully been expressed in E. coli, see Linder M. Et al. (1996).

However, the expression of CBD's in E. coli is not a true extracellular expression and results in an unsatisfactory yield which is too low for industrial scale production of CBD.

U.S. Pat. No. 5,525,195, U.S. Pat. No. 5,536,655, WO 91/17244 and WO 91/10732 discloses expression in a Bacillus host cell of an endoglucanase enzyme which has the catalytically active domain operably linked to a cellulose binding domain.

Accordingly, it is the object of the present invention to provide a method for producing CBD in a high yield, preferably by means of a conventional fermentation technique involving extracellular production of the CBD which in turn makes the use of CBD in industrial applications economically feasible.

SUMMARY OF THE INVENTION

The inventors have now found that it is possible to produce cellulose binding domains (CBDs) by expression in a Bacillus host.

Before the present invention, expression of a CBDs in Bacillus was highly unexpected, since, firstly, cellulose binding domains are known to contain disulfide bridges and, secondly, are potentially susceptible to degradation by proteases produced by the Bacillus host.

Accordingly, in its first aspect the present invention relates to a Bacillus host transformed with a vector comprising a DNA sequence encoding for a cellulose binding domain and capable of expressing the DNA sequence.

In a second aspect, the invention relates to a Bacillus expression vector which carries an inserted DNA sequence encoding for a cellulase binding domain.

Further, in its third aspect, the present invention relates to a method for producing a cellulose binding domain polypeptide in a Bacillus host cell, the method comprising the steps of (a) growing under conditions to overproduce cellulose binding domain in a nutrient medium Bacillus host cells which have been transformed with an expression cassette which includes, as operably joined components, (i) a transcriptional and translational initiation regulatory region, (ii) a DNA sequence encoding the cellulose binding domain polypeptide, (iii) a transcriptional and translational termination regulatory region, wherein the regulatory regions are functional in the host, and (iv) a selection marker gene for selecting transformed host cells; and (b) recovering the cellulose binding domain polypeptide.

DETAILED DESCRIPTION OF THE INVENTION

Figure 1:
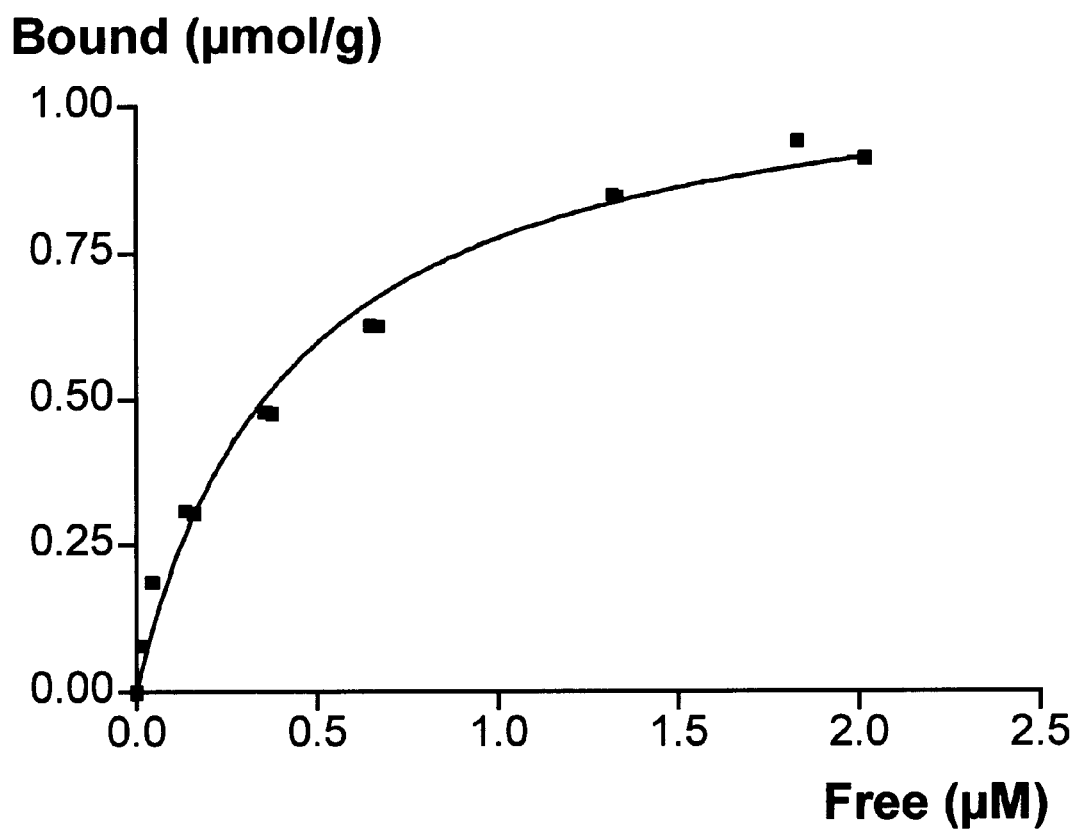

A cellulose binding domain (CBD) is a polypeptide which has high affinity for or binds to water-insoluble forms of cellulose and chitin, including crystalline forms.

CBDs are found as integral parts of large protein complexes consisting of two or more different polypeptide domains, for example in hydrolytic enzymes (hydrolases) which typically are composed of a catalytic domain containing the active site for substrate hydrolysis, and a carbohydrate-binding domain or cellulose-binding domain (CBD) for binding to the insoluble matrix. Such enzymes can comprise more than one catalytic domain and one, two or three CBDs and optionally one or more polypeptide regions linking the CBD(s) with the catalytic domain(s), the latter regions usually being denoted a "linker". Examples of hydrolytic enzymes comprising a CBD are cellulases, xylanases, mannanases, arabinofuranosidases, acetyl esterases and chitinases. CBDs have also been found in algae, e.g. the red alga Porphyra purpurea as a non-hydrolytic polysaccharide-binding protein, see Peter Tomme et al.(1996). However, most of the known CBDs are from cellulases and xylanases.

In this context, the term "cellulose-binding domain" is intended to be understood as defined by Tomme et al., op. cit. This definition classifies more than 120 cellulose-binding domains into 10 families (I–X) which may have different functions or roles in connection with the mechanism of substrate binding. However, during the work resulting in the present invention a hitherto unknown CBD family has been found, cf. example 8 below; and it is anticipated that new family representatives and additional CBD families will appear in the future.

In the protein complex, typically a hydrolytic enzyme, a CBD is located at the N or C termini or is internal.

A monomeric CBD typically consists of more than about 30 and less than about 250 amino acid residues. For example, a CBD classified in Family I consists of 33–37 amino acid residues; a CBD classified in Family IIa consists of 95–108 amino acid residues; and a CBD classified in Family VI consists of 85–92 amino acid residues. Accordingly, the molecular weight of a monomeric CBD will typically be in the range of from about 4 kD to about 40 kD, and usually below about 35 kD.

CBDs may be useful as a single domain polypeptide or as a dimer, a trimer, or a polymer; or as a part of a protein hybrid.

Chimeric protein hybrids

Chimeric protein hybrids are known in the art, see e.g. WO 90/00609, WO 94/24158 and WO 95/16782, and comprise a cellulose binding domain (CBD) from another origin, preferably from another microbial origin, than the chimeric protein as such, which CBD exists as an integral part of the protein. Typically, the chimeric protein hybrids are enzyme hybrids, i.e. contain a catalytic domain together with the binding domain.

Chimeric protein hybrids and enzyme hybrids can be prepared by transforming into a host cell a DNA construct comprising at least a fragment of DNA encoding the cellulose-binding domain (CBD) ligated, with or without a linker, to a DNA sequence encoding the protein or enzyme and growing the host cell to express the fused gene. The recombinant fusion protein or enzyme hybrids may be described by the following formula:

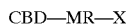

CBD—MR—X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to to about 100 amino acids, more preferably of from 2 to 40 amino acids; and X is an N-terminal or C-terminal region of a polypeptide encoded by the DNA sequence encoding the protein or enzyme.

However, recombinant fusion protein or enzyme hybrids having an internal CBD are also contemplated.

A DNA sequence encoding a CBD from a given organism can be obtained conventionally by using PCR techniques, and, also based on current knowledge, it is possible to find homologous sequences from other organsisms.

It is contemplated that new CBDs can be found by cloning cellulases, xylanases or other plant cell wall degrading enzyme and measure the binding to cellulose. If the enzyme activity is bound to Avicel under the standard condtions described below, it can be assumed that part of the gene codes for a binding domain.

Having obtained the DNA fragment coding for a CBD the DNA gene is inserted in a vector suitable for its expression in Bacillus spp.

For example, cellulose affinity can be measured by using 10 g of Avicel in a 500 ml buffered slurry (buffer: 0.1 sodium phosphate, pH 7.5) which is stirred slowly using a spoon and left swelling for 30 minutes at room temperature. Then the enzyme is added in a ratio of 1 part cellulose binding domain to 150 parts Avicel. This is done on ice which gives optimum binding within 5 to 10 minutes. The Avicel can then be washed and applied directly to SDS-PAGE for visualization of the bound proteins (since the use of SDS and cooking will release the bound proteins). Alternatively, the slurry is packed into a column and washed. The bound protein is eluted, either in ionized water or in a high pH buffer such as triethylamine (pH 11.2; 1% solution), where the pH eluted protein is quickly adjusted to neutral.

Several CBD's have been expressed in *E. coli*, however, none has ever been reported expressed and secreted from Bacillus sp. *E. coli* as an expression host for heterologues proteins has several advantages over Bacillus spp., firstly because *E. coli* has a periplasmic space where proper folding of heterologues expressed genes are possible (for review see for example Hockney, R. C. (1994). Especially the oxidizing potential and the existence of disulfide oxidoreductases in the periplasma is necessary when expressing proteins with a functionality dependent on properly arranged disulfide bridges (Emmanuel Brun et al. (1995). Overproduction, purification and characterization of the cellulose binding domain of the *Erwinia chrysanthemi* secreted endoglucanase EGZ is disclosed in Eur. J. Biochem 231, 142–148, and Ong et al., (1993). Further examples of CBDs with disulfide bonds are: the N-terminal CBD of CelB from *Pseudomonas fluorescens* subsp *cellulosa* (NCIMB 10462) (see the alignment in Tomme P. et al., op. cit., and the N-terminal CBD of CenA from *Cellulomonas fimi* (ATCC 484), N. R. Gilkes et al. (1991).

Furthermore, the periplasma of *E. coli* also acts as in protecting the heterelogously expressed protein towards the action of proteases present in the supernatant as well as the cytoplasm.

It is also known that, when expressing secreted proteins with disulfide bridges in *Bacillus subtilis,* the level of expression drops significantly (van den Berg et al.(1993)).

Another problem with heterologue expression is the proteolytic degradation of the expressed protein. *Bacillus subtilis* is known to express at least 7 different extracellular proteases (Eds. A. L. Sonenshein et al. (1993)).

Especially for CBDs which are highly hydrophobic proteins, the translocation of the protein when expressed in *Bacillus subtilis* could be severely hampered and even cause cell death due to deleterious effects if the protein gets anchored to the cell membrane because of its hydrophobicity.

In its first aspect, the present invention relates to a Bacillus host transformed with a vector comprising a DNA sequence encoding for a CBD and capable of expressing the sequence. Obviously, the expressed polypeptide consists essentially of one or more non-catalytical domains, i.e. the polypeptide does not comprise any catalytically active domain.

In a preferred embodiment, the expressed CBD or CBD-containing polypeptide has a molecular weight (Mw) which is equal to or higher than about 4 kD. Preferably, the Mw is equal to or below about 35 kD, more preferably about 32 kD, even more preferably about 30 kD, especially about 25 kD.

The CBD may be expressed in the form of a single domain polypeptide, i.e. a polypeptide comprising one CBD. Alternatively, the CBD may be expressed in the form of a dimer or trimer or even a polymer, i.e. a polypeptide or protein comprising two, three, or even more than three identical CBD "units".

The CBD can also be expressed as a part of a multidomain polypeptide, the non-CBD part of such a polypeptide being for example one, two or even more domains without catalytic activity.

It is believed that almost any CBD can be expressed according to the present invention, i.e. by means of a transformed Bacillus host. Preferably, such CBDs are expressed which are obtainable from a microorganism or a plant, more preferably from a bacterium or from a fungus.

Examples of CBDs from bacteria include CBDs obtainable from species belonging to one of the following genera: Butyrivibrio, Cellulomonas, Clostridium, Microbispora, Micromonospora, Pseudomonas, Streptomyces, Thermomonospora, Bacillus, Caldocellum, Erwinia, Myxococcus, Cellvibrio, Thermoanaerobacterium, and Thermotoga.

Examples of CBDs from fungi include CBDs obtainable from species belonging to one of the following genera: Agaricus, Dictyostelium, Fusarium, Hunicola, Neocallimastix, Neurospora, Limulus, Penicillium, Phanerochaete, and Trichoderma.

Examples of CBDs obtainable from plants are CBDs from expansins.

The Bacillus host of the present invention is a neutralophilic, an alkalophilic, a mesophllic, or a thermophilic host.

Examples of hosts which are useful in the present invention are hosts from the species *Bacillus subtilis, Bacillus*

*licheniformis, Bacillus megaterium, Bacillus stearothermophilus,* and *Bacillus amyloliquefaciens.* However, it is contemplated that other Bacillus species may also be useful hosts for expression of CBDs As described in further detail below, the host of the invention is transformed with a vector comprising a CBD encoding DNA sequence. Preferably, the vector is integrated into the genome of the host, more preferably it has been amplified on the genome.

In another preferred embodiment of the invention, the vector is present as an expression plasmid, preferably as a multicopy plasmid.

In a second aspect, the present invention relates to a Bacillus expression vector which carries an inserted CBD-encoding DNA sequence. Preferably, the expression cassette of the vector comprises regulatory regions from a Bacillus sp., more preferably are such regulatory regions endogenous to the host.

In a third aspect, the present invention relates to a method for producing a CBD polypeptide, the method comprising the steps of (a) growing under conditions to overproduce cellulose binding domain in a nutrient medium Bacillus host cells which have been transformed with an expression cassette which includes, as operably joined components, (i) a transcriptional and translational initiation regulatory region, (ii) a DNA sequence encoding the cellulose binding domain polypeptide, (iii) a transcriptional and translational termination regulatory region, wherein the regulatory regions are functional in the host, and (iii) a selection marker gene for selecting transformed host cells; and (b) recovering the cellulose binding domain polypeptide.

In its fourth aspect, the present invention relates to a method for optimisation of CBD expression in a Bacillus host, the method comprising the steps of expression in the host of a CBD fused to a reporter molecule; and monitoring the concentration of expressed CBD in the supernatant of the fermented host by measuring the intrinsic property or properties of the reporter molecule.

In a preferred embodiment, the reporter molecule is a Green Fluorescent Protein, and the intrinsic property is fluorescence emission.

In its fifth and sixth aspect, the invention relates to a polypeptide hybrid consisting essentially of one or more cellulose binding domain(s) fused to a green flourescent protein, and to a method of producing such a hybrid by expression in a Bacillus host, growth of the transformed host under conditions whereby the transformed culture is substantially free of untransformed cells; incubation of the transformed culture in a nutrient medium, whereby the hybrid is overproduced; and recovery of the hybrid.

EXPRESSION OF A CBD

Recombinant expression vectors

A recombinant vector comprising a DNA construct encoding the CBD of the invention may be any vector which may conveniently be subjected to recombinant DNA procedures, and the choice of vector will often depend on the host cell into which it is to be introduced. This introduction of vector into the host cell is often referred to as the transformed host cell. Such transformation indicates introduction of DNA into a host cell by using e.g. protoplasts, natural competent cells, transfection, conjugation, electroporation, or any equivalent method. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome in part or in its entirety and replicated together with the chromosome(s) into which it has been integrated.

The vector is preferably an expression vector in which the DNA sequence encoding the CBD of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the CBD.

The promoter may be any DNA sequence which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gen, or the *Bacillus pumilus* xylosidase gene, or the phage Lambda $P_R$ or $P_L$ promoters or the *E. coli* lac, trp or tac promoters. Alternatively, it is possible to design integration vectors such that the DNA encoding the CBD will only become functionally expressed once it is properly integrated into the host genome, e.g. downstream from a resident promoter.

The DNA sequence encoding the CBD of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an CBD of the present invention into the secretory pathway of the host cells, a secretory signal sequence (also known as a leader sequence, prepro sequence or pre sequence) may be provided in the recombinant vector. The secretory signal sequence is joined to the DNA sequence encoding the CBD in the correct reading frame. Secretory signal sequences are commonly positioned 5' to the DNA sequence encoding the CBD. The secretory signal sequence may be that normally associated with the CBD or may be from a gene encoding another secreted protein.

The procedures used to ligate the DNA sequences coding for the present CBD, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op. cit.).

Green Flourescent Protein (GFP) has become a widely used reporter molecule for monotoring gene expression, tracers of cell lineage and as fusion tags for proteins (Crameri et al. (1996); Cubitt et al. (1995); International Patent Application PCT/DK96/00051).

GFP could be fused to CBD's creating a fusion protein having the cellulose binding property as well as the flourescent properties. The expression of this fusion protein could be used to monitor the expressing of CBD's in Bacillus species and hereby be used to optimize expression levels of given CBD's.

EXAMPLES

MATERIALS AND METHODS

Strains:

*Bacillus agaradherens* NCIMB No. 40482 comprises the endoglucanase enzyme encoding DNA sequence of example 8.

*E. coli*: SJ2 (Diderichsen, B. et al. (1990)) Electrocompetent cells prepared and transformed using a Bio-Rad GenePulser™ as recommended by the manufacturer.

*B. subtilis* PL2306. This strain is the *B. subtilis* DN1885 (Diderichsen, B. et al. (1990)) disrupted in the transcriptional unit of the known *Bacillus subtilis* cellulase gene, resulting in cellulase negative cells. Furthermore the strain was disruptedin the aprE and nprE genes (aprE: Stahl and Ferrari (1984)) and (nprE: Yang et al (1984)). The disruptions were performed essentially as described in (Eds. Sonenshein et al. (1993), p.618).

*B. subtilis* PL2304. This strain is the *B. subtilis* DN1885 (Diderichsen, B., op. cit.) disrupted in the transcriptional unit of the known *Bacillus subtilis* cellulase gene, resulting in cellulase negative cells. The disruption was performed essentially as described in (Eds. A. L. Sonenshein, op cit.)

*B. subtilis* ToC46 (Diderichsen, B. et. al., op. cit.).

Plasmids:

pMB100, which is a derivative of pDN1528 (S. Jørgensen et al. (1991). The plasmid is essentially the same as pDN1528, however a SacI sites was for cloning purposes introduced between the stop codon of the amyL gene and its terminator.

pDN1981 (P. L. Jørgensen et al. (1990))

Solutions/Media

TY and LB agar (as described in Ausubel, F. M. et al., 1995).

SB: 32 g Tryptone, 20 g Yeast Extract, 5 g NaCl and 5 ml 1 N NaOH are mixed in sterile water to a final volume of 1 liter. The solution is sterilised by autoclaving for 20 min at 121° C.

10% Avicel: 100 g of Avicel (FLUKA, Switserland) is mixed with sterile water to a final volume of 1 liter, and the 10% Avicel is sterilised by autoclaving for 20 min at 121° C.

Stock solution of Congo red (SIGMA, USA). 1% in ionized water.

Buffer: 0.1 M potassium phosphate, pH 7.5.

General molecular biology methods:

DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al., 1995; Harwood and Cutting, 1990).

Enzymes for DNA manipulations were used according to the specifications of the suppliers.

EXAMPLES 1–3

Isolation of genomic DNA

*Cellulomonas fimi* ATCC484 was grown in TY at 30° C., 250 rpm for 24 hours, cells were harvested by centrifugation.

*Clostridium stercorarium* NCIMB 11754 was grown anaerobically at 60° C. in specified media as recommended by The National Collections of Industrial and Marine Bacteria Ltd. (Scotland). Cells were havested by centrifugation.

*Pseudomonas flourescens* ssp *cellulosa* NCIMB 10462 was grown on TY agar plates for 24 hours at 30° C. Cells were scraped of for isolation of genomic DNA.

From any of the mentioned species, genomic DNA was isolated as described by Pitcher et al. (1989).

Identification of Cellulose Binding Domains present in Glycosyl hydrolases.

Cellulose Binding Domains are classified in ten families according to their amino acid sequences, see Tomme et al. op. cit. Based on the disclosure in this review article three potentially different CBD sequences were choosen as models for expression purposes in *B. subtilis:*

From the family IIa the CBD of *Cellulomonas fimi* (ATCC 484) cellulase CenA (GenBank and SWISS-PROT Accession No. M15823) and the CBD of *Pseudomonas flourescens* (NCIMB 10462) CelB (GenBank and SWISS-PROT Accession No. X52615) were chosen.

From the family VI the CBD-dimer of *Clostridium stercorarium* (NCIMB 11754) XynA (GenBank and SWISS-PROT Accession No. 13325) was chosen.

The SWISS-PROT data obtained describe the position of the putative Cellulose Binding Domains, which information were used to specifically design PCR primers to obtain the DNA fragments encoding the CBD's from the three different bacteria.

At the same time PCR primers were designed as to add extra codons corresponding to amino acids proceding the signal sequence of amyL which is used to direct the CBD's to the exterior of the *Bacillus subtilis* cell.

In vitro amplification of the CBD of *Cellulomonas fimi* (ATCC 484) cellulase CenA Approximately 100 to 200 ng of genomic DNA was PCR amplified in PCR buffer (10 mM Tris-HCl, pH 8.3, 50 mM KCl, 1.5 mM MgCl$_2$, 0.01% (w/v) gelatin) containing 200 µM of each dNTP, 1.5%DMSO (SIGMA,USA), 2.5 units of AmpliTaq polymerase (Perkin-Elmer, Cetus, USA) and 100 pmol of each primer:

CELFIM01U,

5'-CTG CCT CAT TCT GCA GCA GCG GCG GCA   SEQ ID NO:1

AAT CTT AAT GCT CCC GGC TGC CGC GTC GAC

TAC-3'

CELFIM01D,

5'-CTG CCT CAT TGC ATG CAG AGC TCC TAC   SEQ ID NO:2

TAC ACG GTG CCC GTG CAG GTG GTG-3'

Restriction sites PstI and SacI are underlined.

The PCR reactions was performed using a DNA thermal cycler (Landgraf, Germany). One incubation at 94° C. for 5 min followed by thirty cycles of PCR performed using a cycle profile of denaturation at 94° C. for 1 min, annealing at 65° C. for 1 min, and extension at 72° C. for 1 min. Ten-µl aliquots of the amplification product was analyzed by electrophoresis in 1.5% agarose gels (NuSieve, FMC) with ReadyLoad 100 bp DNA ladder (GibcoBRL, Denmark) as a size marker.

In vitro amplification of the CBD of *Pseudomonas flourescens* (NCIMB10462) CelB Approximately 100 to 200 ng of genomic DNA was PCR amplified in HiFidelityTM PCR buffer (Boehringer Mannheim, Germany) supplemented with 200 µM of each dNTP, 2.6 units of HiFidelityTM Expand enzyme mix and 300 pmol of each primer:

PSUPPER,

5'-CGT CCT CAT <u>TCT GCA GCA</u> GCG GCG GCA   SEQ ID NO:3

AAT CTT AAT GCA GCA GTG TGT GAA TAT CGG

G-3'

PSLOWER,

5'-CTG CCT CAT TGC ATG CA<u>G AGC TCC</u> TAC   SEQ ID NO:4

TAT TGT CCA CCG CAA ATC GCC-'

Restriction sites PstI and SacI are underlined.

The PCR reactions was performed using a DNA thermal cycler (Landgraf, Germany). One incubation at 94° C. for 2 min, 30 sec at 60° C. and 45 sec at 72° C. followed by ten cycles of PCR performed using a cycle profile of denaturation at 94° C. for 30 sec, annealing at 60° C. for 30 sec, and extension at 72° C. for 45 sec and twenty cycles of denaturation at 94° C. for 30 sec, 60° C. for 30 sec and 72° C. for 45 sec (at this elongation step 20 sec are added every cycle). Ten-µl aliquots of the amplification product was analyzed by electrophoresis in 1.5% agarose gels (NuSieve, FMC) with ReadyLoad 100 bp DNA ladder (GibcoBRL, Denmark) as a size marker.

In vitro amplification of the CBD-dimer of *Clostridium stercorarium* (NCIMB 11754) XynA.

Approximately 100 to 200 ng of genomic DNA was PCR amplified in HiFidelityTM PCR buffer (Boehringer Mannheim, Germany) supplemented with 200 µM of each dNTP, 2.6 units of HiFidelityTM Expand enzyme mix, and 300 pmol of each primer:

CLOST03U,

5'-CTG CCT CAT <u>TCT GCA GCA</u> GCG GCG GCA   SEQ ID NO:5

AAT CTT AAT CCA ACT CCT GCC CCA TCT CAA

AGC-3'

CLOST03D2,

5'-CTG CCT CAT TGC ATG CA<u>G AGC TCC</u> TAC   SEQ ID NO:6

TAC CAG TCA ACA TTA ACA GGA CCT GAG-3'

Restriction sites PstI and SacI are underlined.

The PCR reactions was performed using a DNA thermal cycler (Landgraf, Germany). One incubation at 94° C. for 2 min, 30 sec at 60° C. and 45 sec at 72° C. followed by ten cycles of PCR performed using a cycle profile of denaturation at 94° C. for 30 sec, annealing at 60° C. for 30 sec, and extension at 72° C. for 45 sec and twenty cyles of denaturation at 94° C. for 30 sec, 60° C. for 30 sec and 72° C. for 45 sec (at this elongation step 20 sec are added every cycle). Ten-µl aliquots of the amplification product was analyzed by electrophoresis in 1.5% agarose gels (NuSieve, FMC) with ReadyLoad 100 bp DNA ladder (GibcoBRL, Denmark) as a size marker.

Cloning by polymerase chain reaction (PCR):

Subcloning of PCR fragments.

Fourty-µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5. Twentyfive-µl of the purified PCR fragment was digested with SacI and PstI, electrophoresed in 1.5% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated DNA fragment was then ligated to PstI SacI digested pMB100 and the ligation mixture was used to transform *B. subtilis* PL2306.

Identification and charaterization of positive clones.

Cells were plated on LB agar plates containing chloramphenicol (6 µg/ml), 0.4% glucose and 10 mM potassium hydrogen phosphate and incubated at 37° C. over night. Next day colonies were restreaked onto fresh LBPG chloramphenicol agar plates and incubated at 37° C. over night. The next day single colonies of each clone were transferred to liquid LB medium containing chloramphenicol (6 µg/ml) and incubated overnight at 37° C. with shaking at 250 rpm.

Plasmids were extracted from the liquid cultures using QIAgen Plasmid Purification mini kit (Qiagen, USA) according to the manufacturer's instructions, however the resuspension buffer was supplemented with 1 mg/ml of Chicken Egg White Lysozyme (SIGMA, USA) prior to lysing the cells at 37° C. for 15 min. Five-µl samples of the plasmids were digested with PstI and SacI. The digestions were checked by gelelectrophoresis on a 1.5% agarose gel (NuSieve, FMC). The appearence of a DNA fragment of the same size as seen from the PCR amplification indicated a positive clone. Three clones were selected each representing a CBD from the three different bacteria mentioned above: MB144 (expressing *C. fimi* CenA-CBD), MB203 (expressing *C. stercorarium* XynA-dimer-CBD) and MB207 (expressing *P. flourescens* ssp. *cellulosa* CelB-CBD).

Nucleotide sequencing the cloned DNA fragment.

Qiagen purified plasmid DNA was sequenced with the Taq deoxy terminal cycle sequencing kit (Perkin Elmer, USA) using the same primers as used above and using an Applied Biosystems 373A automated sequencer according to the manufacturers instructions. Analysis of the sequence data is performed according to Devereux et al.

Expression, secretion and functional analysis of the cloned CBD's

The clones MB144 (expressing *C. fimi* CenA-CBD), MB203 (expressing *C. stercorarium* XynA-dimer-CBD) and MB207 (expressing *P. flourescens* ssp. *cellulosa* CelB-CBD), where all incubated for 20 hours in SB-medium at 37° C. and 250 rpm. 1 ml of cell-free supernatant was mixed with 200 µl of 10% Avicel. The mixture was left for 1 hour incubation at 0° C. After this binding of CBD to Avicel the Avicel with CBD was spun 5 min at 5000 g. The pellet was resuspended in 100 µl of SDS-page buffer, boiled at 95° C. for 5 min, spun at 5000 g for 5 min and 25 µl was loaded on a 18% Laemmli Tris-Glycine, SDS-PAGE NOVEX gel (Novex, USA). The samples were electrophoresed in a Xcell™ Mini-Cell (NOVEX, USA) as recommended by the manufacturer, all subsequent handling of gels including staining with comassie, destaining and drying were performed as described by the manufacturer.

The appearance of protein bands of the expected sizes (MB144 protein band approx. 12 kDa), (MB203 protein band apx. 35 kDa) and (MB207 protein band apx. 12 kDa) indicated expression in *B. subtilis* of functional CBDs.

EXAMPLE 4

Expression and purification of CBD-dimer cloned from *C. stercorarium*

Plasmid isolated from MB203 was used to transform another *Bacillus subtilis* ToC46, thus obtaining a new CBD-dimer expressing clone MB206. Using this strain as the expression host for the CBD-dimer, the clone was incubated in shakeflasks containing SB media (6 ug/ml of chloramphenicol) for 20 hours, at 37° C. and shaking at 250 rpm.

1400 ml of culture fluid supernatant was cooled on ice bath. It was filtrated through Whatman Glass filter F and then sterile filtrated through 0.45 micron millipore Type HVLP.

50 gram of Avicel was suspended in 0.1 M Sodium Phosphate buffer, pH 7.5, at room temperature for 30 min. The supernatant was removed and the Avicel slurry was cooled to 4° C. The clear supernatant was mixed with the Avicel slurry at 4° C. for 30 min.

The Avicel was settled for 10 min and the supernatant removed. The Avicel protein complex was packed in a column and washed with 0.1M sodium phophate buffer, followed by buffer including 0.5M sodium chloride. Finally, the CBD was eluted by deionized water.

A total of 78 ml was eluted containing CBD. The CBD was concentrated after addition of solid sodium chloride to a final concentration of 0.5M on an Amicon cell with a R81P membrane with a cut off of 8 kD.

The concentrated CBD solution (30 ml) had a absorbance at 280 nm of 1.2. The molar extinction coefficient of MB 206 was 42000 corresponding to a protein concentration of 0.82, resulting in a total of 25 mg of highly purified double CBD. Based on SDS-PAGE, the starting material had about 0.1 mg per ml of 29 kD. The final purified product showed only a single band on SDS-PAGE.

EXAMPLE 5

Characterization of a dimerized Fungal CBD, cloned and expressed in *Bacillus subtilis*.

A CBD dimer of fungal origin is constructed by fusing the CBD encoded by the DNA sequence of *Humicola insolens* EGII with the CBD encoded by the DNA sequence of the 43 kDa from *Humicola insolens*.

The DNA sequence encoding *Humicola insolens* EGII CBD and linker is PCR amplified from the plasmid carrying the cDNA of EG II also known as CMC 3 (Dalbøge and Heldt Hansen, 1994) using primers specific for the CBD region and furthermore the antisense primer is designed so as to give the PCR fragment an overhang identical to the DNA fragment encoding the proceeding CBD, the CBD encoded by the gene of the 43 kDa endoglucanase from *H. insolens* which is described in detail in EP-B-0 531 372 and U.S. Pat. No. 5,457,046. The DNA encoding this CBD is PCR amplified from genomic DNA of the *Humicola insulens* described in EP-B-0 531 372.

The two fragments are combined by SOE-PCR (Higuchi et al. (1988)) using the primers:
22857

5'-CTG CCT CAT TCT GCA GCA GCG GCG GCA  SEQ ID NO:7

AAT CCT AAT CAG GGC GGT GCA TGG CAG

CAG-3' and the primer
20622

5'-CTG CCT CAT TGC ATG CAG AGC TCC TAC  SEQ ID NO:8

TAC AGG CAC TGA TGG TAC CAG TC-3'

This PCR fragment is, as a PstI-SacI fragment, ligated to pMB100 and the ligation mixture is used to transform *Bacillus subtilis* PL2306.

The cloned DNA essentially encoding the CBD-dimer can be found in the sequence CBD-EGII-CZ (327 bp):

```
                                        SEQ ID NO:9
GCAAATCTTA ATCAGGGCGG TGCATGGCAG CAGTGTGGTG

GCGTTGGCTT CTCGGGCTCT ACGTCCTGTG TGTCCGGTTA

CACGTGCGTG TACTTGAACG ACTGGTACAG CCAATGCCAG

CCGCAGCCGA CGACGTTACG GACAACAACA ACGCCAGGGG

CAACATCGAC AACAAGGTCA GCCCCGGCTG CCACTTCAAC

CACTCCGGCC GGCTGCACTG CTGAGAGGTG GGCTCAGTGC

GGCGGCAATG GCTGGAGCGG CTGCACCACC TGCGTCGCTG

GCAGCACTTG CACGAAGATT AATGACTGGT ACCATCAGTG

CCTGTAG
``` and the corresponding amino acid sequence (108 aa residues):

```
                                        SEQ ID NO:10
ANLNQGGAWQ QCGGVGFSGS TSCVSGYTCV YLNDWYSQCQ

PQPTTLRTTT TPGATSTTRS APAATSTTPA GCTAERWAQC

GGNGWSGCTT CVAGSTCTKI NDWYHQCL
```

Expression, secretion and functionality of the CBD is characterized as described above.

EXAMPLE 6

Construction of GFP-CBD fusion for CBD expression optimization.

Approximately 100 ng of plasmid DNA pMB144, plasmid is isolated as described above, is PCR amplified in PCR buffer (10 mM Tris-HCl, pH 8.3, 50 mM KCl, 1.5 mM MgCl$_2$, 0.01% (w/v) gelatin) containing 200 μM of each dNTP, 1.5%DMSO (SIGMA,USA), 2.5 units of AmpliTaq polymerase (Perkin-Elmer, Cetus, USA) and 100 pmol of each primer:
C-Fusion1:.

5'-GTC AGT <u>GAA TTC</u> GCA TGC GTC CTT CTT TGT GCT
   TG-3'                                    SEQ ID NO:11

C-Fusion2:

5'-CTC ATA <u>AAG CTT</u> ACG GTG CCC GTG CAG
   GTG GTG-3'                               SEQ ID NO:12

Restriction sites EcoRI and HindIII are underlined.

The PCR reactions is performed using a DNA thermal cycler (Landgraf, Germany). One incubation at 94° C. for 5 min followed by thirty cycles of PCR performed using a cycle profile of denaturation at 94° C. for 1 min, annealing at 60° C. for 1 min, and extension at 72° C. for 1 min. Ten-μl aliquots of the amplification product is analyzed by electrophoresis in 0.7% agarose gels (NuSieve, FMC) with Ready-Load 100 bp DNA ladder (GibcoBRL, Denmark) as a size marker.

The fragment is purified, digested with EcoRI and HindIII, gelpurified and ligated to vector pBR322 (Bolivar et al.(1977), Gene, 2, 95–113.).

The ligation mixture is used to transform SJ2 electrocompetent *E. coli*.

Identification and charaterization of positive clones.

The transformed cells are plated on LB agar plates containing ampicillin (200 µg/ml) and incubated at 37° C. overnight. Next day colonies are rescued by restreaking these onto fresh LB-ampicillin agar plates and incubated at 37° C. over night. The second day single colonies of each clone are transferred to liquid LB medium containing ampicillin (200 µg/ml) and incubated overnight at 37° C. with shaking at 250 rpm.

Plasmids are extracted from the liquid cultures using QIAgen Plasmid Purification mini kit (Qiagen, USA) according to the manufacturer's instructions. Five-µl samples of the plasmids are digested with HindIII and EcoRI. The digestions are checked by gel electrophoresis on a 0.7% agarose gel (NuSieve, FMC).

A derivative of GFP is cloned from the DNA construction of the mutant F64L-S65T-GFP which was constructed as described in international patent application PCT/DK96/00051.

The DNA fragment encoding the F64L-S65T-GFP is cloned as a BamHI-HindIII fragment, In-frame with the CBD encoding DNA cloned in pBR322. Ligation, transformation and identification of a positive clone is done essentially as described above.

This fusion construction is transferred as a EcoRI-BamHI fragment from the E. coli vector to the vector pUB110 vector (Gryczan et al. (1978)). Bacillus subtilis PL2306 is transformed and positive clones are identified by ther ability to fluoresce and by the existence of an Avicel binding F64L-S65T-GFP CBD fusion polypeptide.

The wavelength of the light used for excitation of the F64L-S65T-GFP of this study is 488 nm, this activates the F64L-S65T-GFP to emit light at 510–530 nm.

The flourescence of the supernatant is measured by fluorescence spectroscopy and compared with the flourescence of the supernatant after incubation with Avicel. Furthermore, the flourescent molecule with CBD can be visualized by binding the fusion protein to Avicel, removing excess supernatant and transferring the Avicel to cuvettes for flourescent measuring in a fluorescence spectrometer.

By making serial dilutions of the Avicel bound or non-bound fusion protein, the expression level can be determined, thus making it possible to identify a Bacillus clone expressing relatively higher amounts of CBD.

EXAMPLE 7
Screening using CMC-CongoRed

Recombinant Bacillus clones expressing CBD's can be screened by means of the expression level of the CBD.

In order to find Bacillus strains optimal for expressing a given CBD, the clones of interest are incubated in a suitable medium e.g. as described above in TY and incubated at appropriate growth conditions for 24 hours. Supernatant of the clones are transferred to Agarose-CMC-CongoRed-plates with punched holes, the supernatant with the CBD are left to bind to the CMC for 5 hours at 37° C. When washed 15 min with 2% NaCl solution, the CBD activity can be seen as a clearing zone.

The plate assay can be combined as described below.

Preparation of the gel for use in CBD plate assay: 0.5% CMC and 0.7% agarose (CMC; Carboxymethylcellulose, 7LF from Hercules)(agarose; Litex HSA/HSB) are prepared by moisting the CMC and Agarose with 96% alcohol. 0.1 M potassium phosphate pH 7.5 buffer is added and the mixture is heated to 100° C. until completely dissolved. The solution is left to cool at 60° C. Congo red stock solution is added to a final 5% and plates are poured, 15 ml to a petri dish with 9 cm diameter.

Sample application holes are made with a puncher.

EXAMPLE 8
Identification of a novel CBD defining a new CBD family

The alkaline cellulase cloned iin Bacillus subtilis as described below was expressed by incubating the clone for 20 hours in SB-medium at 37° C. and 250 rpm. The expressed cellulase was shown to contain a CBD by its ability to specifically bind to Avicel.

When left for incubation for a further 20 hours the cellulase was proteolytically cleaved and two specific protein bands appeared on SDS-page one corresponding to the catalytic part of the cellulase approximate molecular weight (MW)35 kD and the other corresponding to a proposed linker and CBD of approximate MW 8 kD.

The CBD was found to be the C-terminal part of the cellulase and the CBD did not match any of the previously described CBD families (Tomme et al., 1995, p. 142–161). Accordingly, this CBD is the first member of a new family. Cloning of the alkaline cellulase from Bacillus agaradherens and expression of the alkaline endoglucanase in Bacillus subtilis.

The nucleotide sequence encoding the alkaline cellulase from Bacillus agaradherens (Deposition No. NCIMB 40482) was cloned by PCR for introduction in an expression plasmid pDN1981.

PCR was performed essentially as described above on 500 ng of genomic DNA, using the following two primers containing NdeI and KpnI restriction sites for introducing the endoglucanase encoding DNA sequence to pDN1981 for expression:

Primer 5: (#20887)

```
5'-GTA GGC TCA GTC ATA TGT TAC ACA      SEQ ID NO:13

TTG AAA GGG GAG GAG AAT CAT GAA AAA

GAT AAC TAC TAT TTT TGT CG-3'
```

Primer 6: (#21318)

```
5'-GTA CCT CGC GGG TAC CAA GCG GCC      SEQ ID NO:14

GCT TAA TTG AGT GGT TCC CAC GGA

CCG-3'
```

After PCR cycling the PCR fragment was purified using QIAquick PCR coulmn Kit (Qiagen, USA) according to the manufacturer's instructions. The purified DNA was eluted in 50 µl of 10 mM Tris-HCl, pH 8.5. Digested with NdeI and KpnI purified and ligated to digested pDN1981. The ligation mixture was used to transform B. subtilis PL2304. Competent cells were prepared and transformed as described by Yasbin et al., (1975).

Isolation and test of Bacillus subtilis transformants.

The transformed cells were plated on LB agar plates containing 10 mg/ml Kanamycin, 0.4% glucose, 10 mM KH2PO4 and 0.1% AZCL HE-cellulose (Megazyme, Australia) and incubated at 37° C. for 18 hours. Endoglucanase positive colonies were identified as colonies surrounded by a blue halo.

Each of the positive transformants were inoculated in 10 ml TY-medium containing 10 mg/ml Kanamycin. After 1 day of incubation at 37° C., 250 rpm, 50 ml supernatant was removed. The endoglucanase activity was identified by adding 50 ml supernatant to holes punctured in the agar of LB agar plates containing 0.1% AZCL HE-cellulose.

After 16 hours incubation at 37° C. blue halos surrounding holes indicated expression of the endoglucanase in *Bacillus subtilis*.

EXAMPLE 9

Assay for selecting CBDs

Preparation of phosphoric acid swollen cellulose (PASC):

5 g Avicel is moistened with water and added 150 ml ice cold 85% phosphoric acid and is weakly stirred on an icebath for 1 hour. Then 500 ml cold acetone is added while stirring. The swollen Avicel (PASC) is filtered on a glass-filter funnel and washed 3 times with 100 ml ice cold acetone and subsequently 2 times with 500 ml water. The PASC is then suspended in 500 ml water and blended to homogeneity using an Ultra Thorax homogenizer. The PASC is stored cold.

Figure 2:
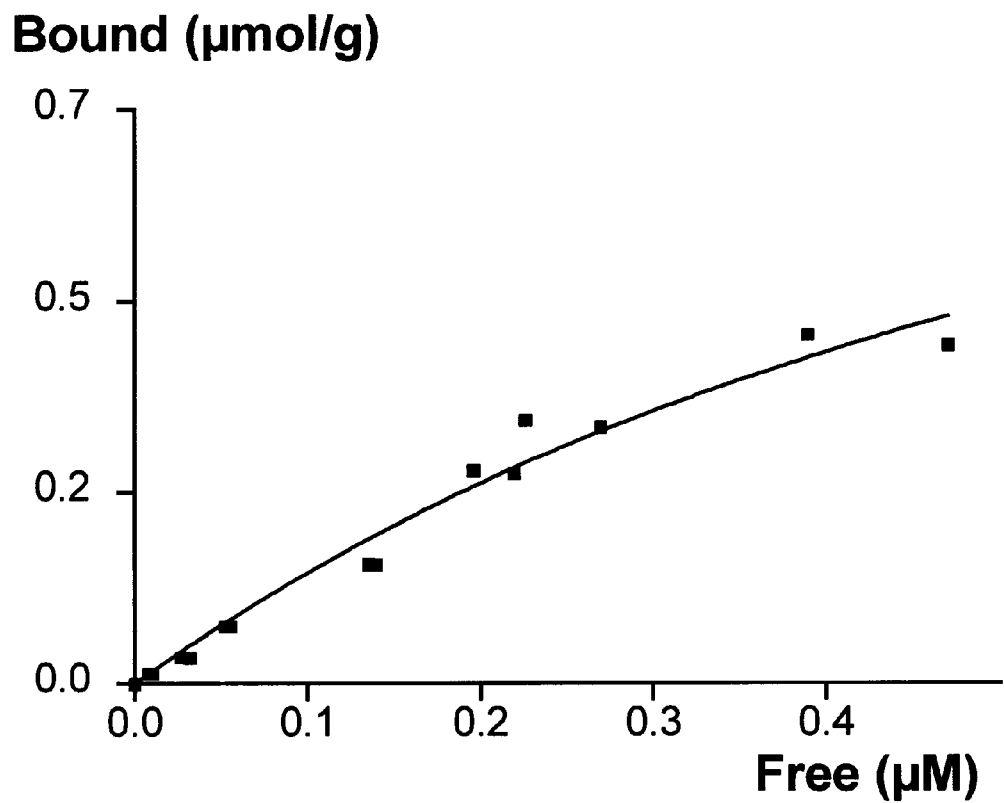

CBD-binding to phosphoric acid swollen cellulose (PASC)—selection of CBDs:

400 ml 10 mg/ml PASC (prepared as described above and washed with 50 mM sodium phosphate, pH 7) in 50 mM sodium phosphate, pH 7 in Eppendorf tubes was mixed with 400 ml of cellulose binding domain (Cel5A CBD or MB206 double CBD) diluted in 50 mM sodium phosphate, pH 7. The concentration of CBD was varied e.g. from 0 mM to around 8 mM for Cel5A CBD. A control series was included without PASC. The samples were incubated for 1 hour at room temperature before centrifuging the samples for 4 minutes at 14000 g. 500 µl of the supernatant was diluted into 2 ml water. The amount of CBD present in the supernatant (free CBD) was then measured by tryptophan fluorescence spectroscopy on the Perkin-Elmer LS50 luminescence spectrometer (excitation at 280 nm and emission at 340 nm) using the fluorescence intensity of the samples without PASC addition as a reference (standard curve). The amount of bound CBD was then calculated as: total CBD (without PASC addition)–free cbd. Thus, a binding isotherm was obtained by plotting the amount of bound CBD per g of PASC as a function of free CBD in solution in mM as shown in FIG. 1 and FIG. 2. The data could be fitted using a simple Langmuir binding model (Bothwell et al., 1995): E(bound)= $(A_{max}*E(free))/(K_d+E(free))$, where E(bound) is the amount of bound CBD in mmol/g PASC and E(free) is the amount of free CBD in mM. $A_{max}$ is the maximum amount of CBD that can be bound to PASC and $K_d$ is the equilibrium constant for the equilibrium E(bound)<<E(free). Thus, the lower the $K_d$ (desorption constant) the stronger the binding. These constants are obtained after fitting the data to the model using algorithms in GraphPad Prizm. Desorption constants found for Cel5A CBD and MB206 double CBD are 0.42 and 0.76 mM respectively (cf. FIG. 1 and FIG. 2).

CBDs of the present invention show desorption constants below 1 mM more preferably below 0.1 mM and most preferably below 10 mM.

LITERATURE LIST

Bothwell, M. K. and Walker, L. P. (1995) Bioresource Technology 53:21–29

Kraulis P., G. M. Clore, M. Nilges, T. A. Jones, G. Pettersson, J. Knowles and A. M. Gronenborn, 1989, "Determination of the three-dimensional structure of the C terminal domain of cellobiohydrolase I from *Trichoderma reesei*. A study using nuclear magnetic resonance and hybrid distance geometry-dynamical simulated annealing" in Biochemistry 28:7241–7257.

Ong E., N. R. Gilkes, R. C. Miller and D. G. Kilburn, 1993, "The cellulose-binding domain (cbdcex) of an exoglucanase from *Cellulomonas fimi*—production in *Escherichia coli* and characterization of the polypeptide" in Biotechnology and Bioengineering. 42:401–409.

Linder M., I. Salovuori, L. Ruohonen and T. T. Teeri, 1996, "Characterization of a double cellulose-binding domain -synergistic high-affinity binding to crystalline cellulose" in Journal of Biological Chemistry 271:21268–21272.

Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996.

Hockney, R. C. (1994) TIBTECH, vol.12, p.456–463.

Emmanuel Brun et al. (1995).

Eur. J. Biochem 231, 142–148.

N. R. Gilkes et al. (1991) Eur. J. Biochem, 202:367–377.

Bertus van den Berg et al., (1993), Introduction of disulfide bonds into *Bacillus subtilis* neutral protease. Protein Engineering, vol.6 no.5, p. 521–527.

Eds. A. L. Sonenshein, J. A. Hoch and Richard Losick (1993) *Bacillus subtilis* and other Gram-Positive Bacteria, American Society for microbiology, p.939 and p. 618.

Andreas Crameri et al. (1996) Improved Green Flourescent Protein by molecular evolution using DNA shuffling, Nature Biotechnology, vol 14, p. 315–319.

Andrew B. Cubitt et al. (1995) Understanding, improving and using flourescent proteins, TIBS, vol 20, p448–455.

Diderichsen, B., Wedsted, U., Hedegaard, L., Jensen, B. R., Sjøholm, C. (1990) Cloning of aldb, which encodes alpha-acetolactate decarboxylase, an exoenzyme from *Bacillus brevis*. J. Bacteriol., 172, 4315–4321.

Stahl, M. L. and E. Ferrari (1984) Replacement of the *Bacillus subtilis* subtilisin structural gene with an In vitro-derived deletion mutation. *J.Bacteriol* 158:411–418.

Yang, M. Y. et al (1984) Cloning ot the neutral protease gene of *Bacillus subtilis* and the use of the cloned gene to create an in vitro-derived deletion mutation. *J. Bacteriol* 160:16–21.

S. Jørgensen et al. (1991) Journal of Bacteriology, vol. 173, No., p-559–567.

P. L. Jørgensen, C. K. Hansen, G. B. Poulsen and B. Diderichsen (1990) In vivo genetic engineering: homologues recombination as a tool for plasmid construction, Gene, 96, p37–41.

Ausubel, F. M. et al. (eds.) "Current protocols in Molecular Biology". John Wiley and Sons, 1995

Sambrook et al. (1989) Molecular cloning: A laboratory manual, Cold Spring Harbor lab., Cold Spring Harbor, N.Y.

Harwood, C. R., and Cutting, S. M. (eds.) "Molecular Biological Methods for Bacillus". John Wiley and Sons, 1990.

Pitcher, D. G., Saunders, N. A., Owen, R. J. (1989). Rapid extraction of bacterial genomic DNA with guanidium thiocyanate. Lett. Appl. Microbiol., 8, 151–156).

Devereux et al.

Dalbøge, H. and H. P. Heldt Hansen. 1994. A novel method for efficient expression cloning of fungal enzyme genes, Molecular & General Genetics. 243:253–260.

Higuchi et al. (1988) NAR 16:7351–7367.

Gryczan, T. J. et al. (1978) Journal of Bacteriology, 134, p.318–329.

Tomme P., R. A. Warren, R. C. Miller, Jr., D. G. Kilburn and N. R. Gilkes. 1995. Cellulose-Binding Domains: Classification and Properties. In: Saddler J. N. and M. H. Penner, eds. Enzymatic Degradation of Insoluble Carbohydrates. Washington, DC, American Chemical Society. page 142–161.

Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296–304.

What is claimed is:

1. A Bacillus host cell capable of secreting a cellulose-binding polypeptide, said cell comprising a vector comprising a DNA sequence encoding said cellulose-binding domain polypeptide fused in frame to an aminoterminal signal sequence, wherein said polypeptide contains one or more cellulose-binding domains and lacks a catalytic domain.

2. The host of claim 1, wherein the DNA sequence is of another origin than Bacillus.

3. The host of claim 1 which is capable of expressing the cellulose-binding domain polypeptide as a single polypeptide chain.

4. The host of claim 1, wherein the cellulose binding domain has an apparent molecular weight as determined by SDS-PAGE in the range of from 4 kD to 35 kD.

5. The host of claim 4, wherein the cellulose-binding domain polypeptide has an apparent molecular weight as determined by SDS-PAGE not higher than 30 kD.

6. The host of claim 1, wherein the vector comprises a DNA sequence encoding a single cellulose binding domain.

7. The host of claim 1, wherein the vector comprises a DNA sequence encoding a dimeric or a trimeric cellulose binding domain.

8. The host of claim 1, wherein the cellulose binding domain is obtainable from a microorganism or from a plant.

9. The host of claim 8, wherein the microorganism is a bacterium selected from the group consisting of the genera Butyrivibrio, Cellulomonas, Clostridium, Microbispora, Micromonospora, Pseudomonas, Streptomyces, Thermomonospora, Bacillus, Caldocellum, Erwinia, Myxococcus, Cellvibrio, Thermoanaerobacterium, and Thermotoga.

10. The host of claim 8, wherein the microorganism is a fungus selected from the group consisting of the genera Agaricus, Dictyostelium, Fusarium, Humicola, Neocallimastix, Neurospora, Limulus, Penicillium, Phanerochaete, and Trichoderma.

11. The Bacillus host of claim 1 which is neutralophilic, alkalophilic, mesophilic or thermophilic.

12. The Bacillus host of claim 11 which is selected from the group consisting of the species *Bacillus subtilis, Bacillus licheniformis, Bacillus megaterium, Bacillus stearothermophilus,* and *Bacillus amyloliquefaciens.*

13. The host of claim 1, wherein the vector is integrated into the genome of the host cell.

14. The host of claim 1, wherein the vector is present as an expression plasmid.

15. The host of claim 1, wherein the vector has been amplified on the genome or the expression plasmid is a multicopy plasmid.

16. A Bacillus expression vector which carries an inserted DNA sequence encoding a cellulose binding domain.

17. The vector of claim 16 in which the expression cassette comprises regulatory regions from a Bacillus species.

18. The vector of claim 17, wherein the Bacillus regulatory regions are endogeneous to the host.

19. A method for producing in a Bacillus host cell a polypeptide containing a cellulose binding domain and lacking a catalytic domain, the method comprising the steps of:

(a) growing in a nutrient medium Bacillus host cells which have been transformed with an expression cassette which includes, as operably joined components, (i) a transcriptional and translational initiation regulatory region, (ii) a DNA sequence encoding said polypeptide, (iii) a transcriptional and translational termination regulatory region, wherein the regulatory regions are functional in the host, and (iv) a selection marker gene for selecting transformed host cells, wherein said growing results in overproduction of said polypeptide; and (b) recovering said polypeptide.

20. The method of claim 19 wherein the produced cellulose binding domain polypeptide has an apparent molecular weight as determined by SDS-PAGE in the range of from 4 kD to 35 kD.

* * * * *

```
                            SEQUENCE LISTING

<160> NUMBER OF SEQ ID NOS: 14

<210> SEQ ID NO 1
<211> LENGTH: 60
<212> TYPE: DNA
<213> ORGANISM: Cellulomonas fimi

<400> SEQUENCE: 1
ctgcctcatt ctgcagcagc ggcggcaaat cttaatgctc ccggctgccg cgtcgactac        60

<210> SEQ ID NO 2
<211> LENGTH: 51
<212> TYPE: DNA
<213> ORGANISM: Cellulomonas fimi

<400> SEQUENCE: 2
ctgcctcatt gcatgcagag ctcctactac acggtgcccg tgcaggtggt g                 51

<210> SEQ ID NO 3
<211> LENGTH: 58
<212> TYPE: DNA
<213> ORGANISM: Pseudomonas flourescens

<400> SEQUENCE: 3
cgtcctcatt ctgcagcagc ggcggcaaat cttaatgcag cagtgtgtga atatcggg          58

<210> SEQ ID NO 4
<211> LENGTH: 48
<212> TYPE: DNA
<213> ORGANISM: Pseudomonas flourescens

<400> SEQUENCE: 4
ctgcctcatt gcatgcagag ctcctactat tgtccaccgc aaatcgcc                     48

<210> SEQ ID NO 5
<211> LENGTH: 60
<212> TYPE: DNA
<213> ORGANISM: Clostridium stercorarium

<400> SEQUENCE: 5
ctgcctcatt ctgcagcagc ggcggcaaat cttaatccaa ctcctgcccc atctcaaagc        60

<210> SEQ ID NO 6
<211> LENGTH: 54
<212> TYPE: DNA
<213> ORGANISM: Clostridium stercorarium

<400> SEQUENCE: 6
ctgcctcatt gcatgcagag ctcctactac cagtcaacat taacaggacc tgag              54

<210> SEQ ID NO 7
<211> LENGTH: 57
<212> TYPE: DNA
<213> ORGANISM: Humicola insolens

<400> SEQUENCE: 7
ctgcctcatt ctgcagcagc ggcggcaaat cttaatcagg gcggtgcatg gcagcag           57
```

```
<210> SEQ ID NO 8
<211> LENGTH: 50
<212> TYPE: DNA
<213> ORGANISM: Humicola insolens

<400> SEQUENCE: 8
ctgcctcatt gcatgcagag ctcctactac aggcactgat ggtaccagtc            50

<210> SEQ ID NO 9
<211> LENGTH: 327
<212> TYPE: DNA
<213> ORGANISM: Humicola insolens

<400> SEQUENCE: 9
gcaaatctta atcagggcgg tgcatggcag cagtgtggtg gcgttggctt ctcgggctct    60
acgtcctgtg tgtccggtta cacgtgcgtg tacttgaacg actggtacag ccaatgccag   120
ccgcagccga cgacgttacg gacaacaaca acgccagggg caacatcgac aacaaggtca   180
gccccggctg ccacttcaac cactccggcc ggctgcactg ctgagaggtg ggctcagtgc   240
ggcggcaatg gctggagcgg ctgcaccacc tgcgtcgctg gcagcacttg cacgaagatt   300
aatgactggt accatcagtg cctgtag                                      327

<210> SEQ ID NO 10
<211> LENGTH: 108
<212> TYPE: PRT
<213> ORGANISM: Humicola insolens

<400> SEQUENCE: 10

Ala Asn Leu Asn Gln Gly Gly Ala Trp Gln Gln Cys Gly Gly Val Gly
 1               5                  10                  15

Phe Ser Gly Ser Thr Ser Cys Val Ser Gly Tyr Thr Cys Val Tyr Leu
                20                  25                  30

Asn Asp Trp Tyr Ser Gln Cys Gln Pro Gln Pro Thr Thr Leu Arg Thr
             35                  40                  45

Thr Thr Thr Pro Gly Ala Thr Ser Thr Thr Arg Ser Ala Pro Ala Ala
     50                  55                  60

Thr Ser Thr Thr Pro Ala Gly Cys Thr Ala Glu Arg Trp Ala Gln Cys
 65                  70                  75                  80

Gly Gly Asn Gly Trp Ser Gly Cys Thr Thr Cys Val Ala Gly Ser Thr
                 85                  90                  95

Cys Thr Lys Ile Asn Asp Trp Tyr His Gln Cys Leu
            100                 105

<210> SEQ ID NO 11
<211> LENGTH: 35
<212> TYPE: DNA
<213> ORGANISM: Humicola insolens

<400> SEQUENCE: 11
gtcagtgaat tcgcatgcgt ccttctttgt gcttg                             35

<210> SEQ ID NO 12
<211> LENGTH: 33
<212> TYPE: DNA
<213> ORGANISM: Humicola insolens

<400> SEQUENCE: 12
ctcataaagc ttacggtgcc cgtgcaggtg gtg                               33
```

-continued

```
<210> SEQ ID NO 13
<211> LENGTH: 71
<212> TYPE: DNA
<213> ORGANISM: Bacillus agaradherens

<400> SEQUENCE: 13
gtaggctcag tcatatgtta cacattgaaa ggggaggaga atcatgaaaa agataactac      60
tatttttgtc g                                                          71

<210> SEQ ID NO 14
<211> LENGTH: 51
<212> TYPE: DNA
<213> ORGANISM: Bacillus agaradherens

<400> SEQUENCE: 14
gtacctcgcg ggtaccaagc ggccgcttaa ttgagtggtt cccacggacc g               51
```